US007670676B2

(12) United States Patent
Horiishi et al.

(10) Patent No.: US 7,670,676 B2
(45) Date of Patent: Mar. 2, 2010

(54) PHARMACEUTICAL RAW MATERIAL

(75) Inventors: Nanao Horiishi, Yokohama (JP);
Toshiyuki Hakata, Hiroshima (JP);
Hirofumi Kawasaki, Hiroshima-ken (JP); Shinji Uemoto, Hiroshima (JP);
Hiromitsu Misawa, Hiroshima (JP);
Seiichi Takahashi, Tokyo (JP)

(73) Assignee: Toda Kogyo Corporation, Hiroshima-shi, Hiroshima-ken (JP)

( * ) Notice: Subject to any disclaimer, the term of this patent is extended or adjusted under 35 U.S.C. 154(b) by 13 days.

(21) Appl. No.: 11/451,597

(22) Filed: Jun. 13, 2006

(65) Prior Publication Data
US 2006/0287404 A1 Dec. 21, 2006

(30) Foreign Application Priority Data

Jun. 15, 2005 (JP) ............................ 2005-175801
Jun. 15, 2005 (JP) ............................ 2005-175802

(51) Int. Cl.
*B32B 19/00* (2006.01)
*B32B 5/16* (2006.01)
(52) U.S. Cl. ...................... 428/357; 428/372; 428/402

(58) Field of Classification Search ....................... None
See application file for complete search history.

(56) References Cited
U.S. PATENT DOCUMENTS 4,101,435 A * 7/1978 Hasegawa et al. ......... 252/62.53
5,055,288 A * 10/1991 Lewis et al. ................ 424/9.32

* cited by examiner

*Primary Examiner*—Sheeba Ahmed
(74) *Attorney, Agent, or Firm*—Nixon & Vanderhye P.C.

(57) ABSTRACT

There are provided a pharmaceutical raw material capable of exhibiting a uniform functionality and producing magnetic particle-containing drugs for diagnosis and medical treatments with a high reproducibility. The pharmaceutical raw material comprises a monodisperse colloid sterile aqueous solution of magnetic iron oxide fine particles having an average particle diameter of 5 to 30 nm, a saturation magnetization of 50 to 90 $Am^2/kg$ and a coercive force of 0.1 to 1.6 kA/m. The pharmaceutical raw material can be produced by forming magnetic iron oxide fine particles in the form of a colloid aqueous solution, purifying the resultant colloid aqueous solution of superparamagnetic iron oxide particles by water-washing and removing water-soluble salts by-produced upon the reaction from the reaction solution by an ordinary method, and replacing a dispersing medium of the purified colloid aqueous solution with ultrapure water.

9 Claims, No Drawings

PHARMACEUTICAL RAW MATERIAL

BACKGROUND OF THE INVENTION

The present invention relates to a pharmaceutical raw material containing magnetic particles, and more particularly, to a pharmaceutical raw material containing magnetic particles, which is used for preparing medicines or drugs for drug delivery system as a method for delivering drugs (hereinafter referred to merely as "DDS"), CT (computed tomography) diagnosis used in roentgen and MRI (magnetic resonance), and medical treatments such as thermotherapy in medical technology fields. More specifically, the present invention relates to a pharmaceutical raw material containing magnetic particles, which is capable of improving a delivery directivity of drugs containing magnetic particles to lesion tissues or cells, contrast sensitivity upon diagnosis using CT, exothermic property upon thermotherapy, etc.

In recent years, there have been studied drugs containing magnetic particles, which are used in the form of a composite material composed of magnetic iron oxide fine particles as a magnetic material, and a biocompatible substance such as a phospholipid, a protein and a water-soluble polymer (Japanese Patent Application Laid-open (KOKAI) Nos. 3-128331 (1991), 4-52202(1992), 7-122410(1995) and 11-106391 (1999) and Japanese Translation of International Patent Application Laid-open (KOHYO) No. 8-500700(1996)).

Also, in order to prepare a monodisperse aqueous solution of magnetic iron oxide fine particles, there are known a method of coating the surface of the respective particles with a surface-treating agent such as a surfactant (Japanese Patent Application Laid-open (KOKAI) No. 1-4002(1989)), a method of coating the surface of the respective particles with an inorganic material such as Al and Si (Japanese Patent Application Laid-open (KOKAI) No. 5-310429(1993)), a method of coating the surface of the respective particles with an organometallic polymer (Japanese Translation of International Patent Application Laid-open (KOHYO) No. 8-500700 (1996)), etc.

Although these methods relate to techniques concerning magnetic particles-containing drugs using magnetic iron oxide particles, there are mainly described techniques for imparting a modifying function to the magnetic particles. Therefore, these methods may fail to sufficiently analyze the relation of characteristic factors between particle properties such as particle size or magnetic properties of the magnetic iron oxide fine particles and properties of the drugs containing magnetic particles.

In particular, it has been conventionally difficult to uniformly disperse and support the magnetic iron oxide fine particles on the biocompatible substance owing to magnetic coagulation inherent to the iron oxide particles. For this reason, hitherto, it has been required to use magnetic iron oxide particles having a large particle size.

In the case where such magnetic iron oxide particles having a large particle size are used for medical treatments, there is a high possibility that the iron oxide particles remain in vivo after the medical treatments, thereby failing to ensure a sufficient safety upon use thereof.

In consequence, it has been strongly required to develop a pharmaceutical material capable of not only exhibiting a uniform functionality, for example, a delivering capability for reagents, contrast sensitivity, exothermic property, etc., but also producing magnetic particles-containing drugs for diagnosis and medical treatments, which can exhibit a sufficient function, with a high reproducibility.

As described above, in order to produce such magnetic material-containing drugs having uniform characteristics with a high reproducibility, it is inevitably required to uniformly disperse and mix the biocompatible substance and the magnetic iron oxide fine particles with each other upon the drug-making process. For this purpose, it is also required that the magnetic iron oxide fine particles contained in the pharmaceutical raw material have a fine and uniform particle size, and the pharmaceutical raw material is in the form of a dispersed colloid aqueous solution containing the magnetic iron oxide fine particles.

However, when the magnetic iron oxide fine particles are dispersed in the solution using a surface-treating agent such as a surfactant, the surface-treating agent used tends to remain and be mixed in the resultant magnetic material-containing drugs, resulting in not only adverse influence on safety to living organisms, but also difficulty in mixing with the biocompatible substance. In addition, the removal of the surface-treating agent from the obtained drugs requires complicated procedures.

Under the circumstances of the above conventional problems, as a result of the present inventors' earnest study for solving the above problems, by noticing magnetic iron oxide fine particles as magnetic particles for drugs, it has been found that a monodisperse colloid aqueous solution of superparamagnetic iron oxide particles can exhibit a good dispersion stability under specific conditions. The present invention has been attained on the basis of the above finding.

SUMMARY OF THE INVENTION

An object of the present invention is to provide a monodisperse colloid sterile aqueous solution of magnetic iron oxide fine particles having a uniform particle size without using any surface-treating agent.

Another object of the present invention is to provide a dispersed colloid sterile aqueous solution containing flocculated particles composed of magnetic iron oxide fine particles having a uniform particle size without using any surface-treating agent.

The other object of the present invention is to provide a dried product composed of magnetic iron oxide fine particles having a uniform particle size without using any surface-treating agent.

To accomplish the aims, in a first aspect of the present invention, there is provided a pharmaceutical raw material comprising magnetic iron oxide fine particles having an average particle diameter of 5 to 30 nm and ultrapure water, the said material being in the form of a monodisperse colloid sterile aqueous solution of the magnetic iron oxide fine particles.

In a second aspect of the present invention, there is provided a pharmaceutical raw material comprising flocculated particles composed of primary particles of magnetic iron oxide fine particles having an average particle diameter of 5 to 30 nm and ultrapure water, the said flocculated particles having a particle diameter of 30 to 200 nm and the said pharmaceutical raw material being in the form of a colloid sterile aqueous solution in which the flocculated particles composed of the magnetic iron oxide fine particles are dispersed.

In a third aspect of the present invention, there is provided a pharmaceutical raw material comprising a dried product produced from a (mono)disperse colloid sterile aqueous solution containing magnetic iron oxide fine particles having an average particle diameter of 5 to 30 nm and ultrapure water.

In a fourth aspect of the present invention, there is provided a method of using a dried product or a frozen product produced from a colloid sterile aqueous solution containing magnetic iron oxide fine particles having an average particle diameter of 5 to 30 nm and ultrapure water, as a pharmaceutical raw material.

DETAILED DESCRIPTION OF THE INVENTION

The present invention is described in detail below.

First, the magnetic iron oxide fine particles and the ultrapure water constituting the pharmaceutical raw material of the present invention are described.

The magnetic iron oxide fine particles used in the present invention have a primary particle diameter of 5 to 30 nm, preferably 5 to 20 nm and more preferably 5 to 10 nm. When the primary particle diameter is less than 5 nm, the magnetic iron oxide fine particles tend to be amorphous. When the primary particle diameter is more than 30 nm, the magnetic iron oxide fine particles tend to be magnetically coagulated together. In addition, the magnetic iron oxide fine particles having a primary particle diameter of not more than 10 nm are more preferred since such particles exhibit a superparamagnetism, and therefore, have a coercive force of zero.

The magnetic iron oxide fine particles used in the present invention are in the form of a spinel-type ferromagnetic material represented by the formula:

$$MOFe_2O_3$$

wherein M is a divalent metal.

Specific examples of the divalent metal M may include Fe and/or Mg.

When M is Fe, the magnetic iron oxide fine particles have a composition represented by the formula:

$$Fe_xOFe_2O_3$$

wherein x is a number of 0 to 1.

The number x in the above composition formula represents a content of the divalent iron. When x is 1, the composition is represented by the formula: $FeOFe_2O_3$, namely magnetite. When x is 0, the composition is represented by the formula: $\gamma\text{-}Fe_2O_3$, namely maghemite. Also, in the case where x is more than 0 and less than 1 ($0<x<1$), the composition represents a spinel-type iron oxide which is also magnetic iron oxide. In the present invention, there may be used these superparamagnetic iron oxide particles.

When M represents Fe and Mg, the total amount of Fe and Mg is usually not more than 1 mol based on 1 mol of $Fe_2O_3$. The use of Mg is suitable because of a good biocompatibility thereof.

Meanwhile, other divalent metals may also be used according to applications and purposes.

Also, the magnetic iron oxide fine particles may be in the form of a composite material obtained by mixing the magnetic iron oxide fine particles with a phospholipid, a polysaccharide, a protein or dextrins.

The ultrapure water used in the present invention contains a substantially no dissolved oxygen, and therefore, is as close as theoretical water having a purity of 100%, i.e., $H_2O$. In general, the ultrapure water is water having a resistivity of usually not less than 10 MΩ·cm (i.e., an electrical conductivity of usually not more than 0.1 μS/cm, preferably not more than $6\times10^{-2}$ μS/cm).

The ultrapure water may be produced by treating water treated in ordinary water purifying plants (tap water) using an ion-exchange apparatus or a pure water production apparatus with reverse osmosis membrane to remove inorganic ions, etc., therefrom, passing the thus treated water through a deaeration apparatus to remove dissolved gases such as dissolved oxygen therefrom, and then subjecting the resultant water to sterilization, desalting, and removal and purification of solid particles, etc., using an ultrafilter.

The concentration of the magnetic iron oxide fine particles contained in the pharmaceutical raw material of the present invention is usually 5 to 50 mg/mL and preferably 10 to 40 mg/mL. When the concentration of the magnetic iron oxide fine particles is more than 50 mg/mL, the resultant particles tend to be coagulated together due to the increased influence of van der Waals force exerted between the particles. When the concentration of the magnetic iron oxide fine particles is less than 5 mg/mL, the pharmaceutical raw material having such a low content of the magnetic iron oxide fine particles tends to be unsuitable for actual use.

The term "sterile aqueous solution" used in the present invention means an aqueous solution which is proved to be a negative when subjected to any of a toxicity test and an endotoxin test. More specifically, the sterile aqueous solution has a plate count of usually less than $1\times10^{-6}$/unit, and contains an endotoxin in an amount of usually not more than 0.25 EU/mL.

(A) Next, the pharmaceutical raw material according to the first aspect of the present invention, which comprises magnetic iron oxide fine particles having an average particle diameter of 5 to 30 nm and ultrapure water, and which is in the form of a monodisperse colloid sterile aqueous solution of the magnetic iron oxide fine particles, is explained.

The term "monodisperse colloid" used herein means that the magnetic iron oxide fine particles contained in the aqueous solution have a so-called narrow particle size distribution. More specifically, the variation coefficient calculated by the formula:

$$\text{Variation coefficient (\%)} = \{(\text{standard deviation of particle size distribution})/(\text{average particle diameter})\} \times 100,$$

is usually not more than 15%, preferably not more than 12%, more preferably not more than 10%. When the variation coefficient is more than 15%, the magnetic iron oxide fine particles may fail to exhibit a uniform particle size distribution.

The magnetic iron oxide fine particles used in the present invention have a coercive force of usually 0 to 1.6 kA/m, preferably 0.05 to 1.2 kA/m. When the coercive force is as large as more than 1.6 kA/m, the resultant particles tend to be magnetically coagulated together due to a residual magnetization generated therein. The magnetic iron oxide fine particles used in the present invention have a saturation magnetization of usually 50 to 90 $Am^2/kg$, preferably 55 to 85 $Am^2/kg$. When the saturation magnetization is less than 50 $Am^2/kg$, the resultant particles tend to lack in magnetic properties. When the saturation magnetization is more than 90 $Am^2/kg$, the resultant particles may fail to form spinel-type iron oxide particles.

The pharmaceutical raw material according to the first aspect of the present invention has a pH of usually not less than 7.0, preferably 9.0 to 11.0.

The pharmaceutical raw material according to the first aspect of the present invention preferably has an electrical conductivity of usually not less than 100 μS.

(B) Next, the pharmaceutical raw material according to the second aspect of the present invention which comprises flocculated particles composed of primary particles of magnetic iron oxide fine particles having an average particle diameter of 5 to 30 nm, and ultrapure water, wherein the flocculated particles have a particle diameter of 30 to 200 nm, and which pharmaceutical raw material is in the form of a colloid sterile aqueous solution in which the flocculated particles composed of magnetic iron oxide fine particles are dispersed, is explained.

The flocculated magnetic iron oxide fine particles used in the second aspect of the present invention have a particle diameter of usually 30 to 200 nm, preferably 50 to 150 nm. When the particle diameter of the flocculated magnetic iron oxide fine particles is less than 30 nm, the resultant particles tend to be deteriorated in exothermic property due to an alternating field when used for thermotherapy of cancers. On the other hand, when the particle diameter of the flocculated magnetic iron oxide fine particles is more than 200 nm, it may be difficult to egest the dosed particles from in vivo.

As to the particle size distribution of the primary particles of the magnetic iron oxide fine particles used in the second aspect of the present invention, the variation coefficient calculated by the formula:

Variation coefficient (%)={(standard deviation of particle size distribution)/(average particle diameter)}×100, is preferably not more than 10%, more preferably not more than 8%. When the variation coefficient is more than 10%, the resultant particles may fail to exhibit a good dispersibility in water, so that there tends to arise such a problem that the magnetic particles are precipitated with the passage of time.

The magnetic iron oxide fine particles used in the second aspect of the present invention is preferably a superparamagnetic material, and have a coercive force of usually 0 to 6.0 kA/m, preferably 0.05 to 4.0 kA/m. When the coercive force is as large as more than 6.0 kA/m, the resultant particles tend to be magnetically coagulated together due to a residual magnetization generated therein.

The magnetic iron oxide fine particles used in the second aspect of the present invention have a saturation magnetization of usually 35 to 90 $Am^2/kg$, preferably 50 to 85 $Am^2/kg$. When the saturation magnetization is less than 35 $Am^2/kg$, the resultant particles tend to lack in magnetic properties. When the saturation magnetization is more than 90 $Am^2/kg$, the resultant particles may fail to form spinel-type iron oxide particles.

The pharmaceutical raw material according to the second aspect of the present invention has a pH of usually not less than 9.0, preferably 9.0 to 11.0.

The pharmaceutical raw material according to the second aspect of the present invention preferably has a zeta potential of usually not more than −20 mV, preferably not more than −30 mV.

The pharmaceutical raw material according to the second aspect of the present invention preferably has an electrical conductivity of usually 50 to 400 μS.

In the present invention, as the magnetic iron oxide fine particles, there may also be used a composite material composed of the magnetic iron oxide fine particles and a phospholipid, a polysaccharide, a protein or dextrins.

(C) Next, the pharmaceutical raw material according to the third aspect of the present invention, which comprises a dried product produced by freeze-drying a monodisperse colloid sterile aqueous solution comprising the magnetic iron oxide fine particles having an average particle diameter of 5 to 30 nm and ultrapure water, is explained.

As to the particle size distribution of the magnetic iron oxide fine particles used in the third aspect of the present invention, the variation coefficient calculated by the formula:

Variation coefficient (%)={(standard deviation of particle size distribution)/(average particle diameter)}×100, is preferably not more than 10%, more preferably not more than 8%. When the variation coefficient is more than 10%, the resultant particles may fail to exhibit a good dispersibility in water, so that there may tend to arise such a problem that the magnetic particles are precipitated with the passage of time.

The magnetic iron oxide fine particles used in the third aspect of the present invention is preferably a superparamagnetic material, and have a coercive force of usually 0 to 6.0 kA/m, preferably 0.05 to 4.0 kA/m. When the coercive force is as high as more than 6.0 kA/m, the resultant particles tend to be magnetically coagulated together due to a residual magnetization generated therein.

The magnetic iron oxide fine particles used in the third aspect of the present invention have a saturation magnetization of usually 35 to 90 $Am^2/kg$, preferably 50 to 85 $Am^2/kg$. When the saturation magnetization is less than 35 $Am^2/kg$, the resultant particles tend to lack in magnetic properties. When the saturation magnetization is more than 90 $Am^2/kg$, the resultant particles may fail to form spinel-type iron oxide particles.

(D) The method according to the fourth aspect of the present invention, comprises using a dried product or frozen product produced from colloid aqueous solution containing the magnetic iron oxide fine particles as a pharmaceutical raw material, is explained.

The dried product used is produced by freeze-drying the colloid aqueous solution as defined in the above first or second aspect.

The frozen product used is produced by freezing the colloid aqueous solution as defined in the above first or second aspect.

Next, the process for producing the pharmaceutical raw material according to the present invention is explained.

The process for producing the monodisperse colloid aqueous solution of the magnetic iron oxide fine particles includes the following three steps.

(1) Step of producing the magnetic iron oxide fine particles;

(2) Step of purifying the colloid aqueous solution of the magnetic iron oxide fine particles by water-washing the colloid aqueous solution by an ordinary method to remove water-soluble salts by-produced upon the reaction from a reaction mother liquor; and (3) Step of replacing a dispersing medium of the thus purified colloid aqueous solution with ultrapure water.

The magnetic iron oxide fine particles used in the present invention may be produced by an aqueous solution reaction method using an aqueous iron salt solution and alkali (wet method), or a method of heat-reducing iron oxide particles in a reducing gas such as hydrogen (dry method).

Among the above methods for producing the magnetic iron oxide fine particles, there may be generally used the wet method which is generally referred to as a co-precipitation method or an oxidation reaction method of ferrous hydroxide colloid.

In the co-precipitation method, for example, an aqueous alkali solution is added under stirring to a mixed aqueous solution containing 1 mol of an aqueous ferrous (Fe(II)) salt solution and 2 mol of an aqueous ferric (Fe(III)) salt solution under not less than 5 to less than 50 mg/mL of a concentration of sum of a divalent metal salt including ferric (Fe(III)) salt, Mg salt, etc. and ferric (Fe(III)) salt, to cause a co-precipitation reaction between Fe(II) and 2Fe(III), thereby producing magnetite particles as black spinel-type magnetic iron oxide. In the case where a divalent metal other than Fe, for example, Mg, is additionally used in the above co-precipitation reaction, Mg-containing spinel-type magnetic iron oxide particles are produced. In addition, since the particle size of the resultant particles can be controlled by varying the reaction conditions such as concentrations of the iron salts and the mixing temperature, the desired magnetic iron oxide fine particles can be produced by suitably combining these reaction conditions.

The oxidation reaction method of the ferrous hydroxide colloid means such a reaction including a step of adding an aqueous alkali solution to an aqueous ferrous salt solution to produce ferrous hydroxide colloid, and a step of passing an oxygen-containing gas such as air through an aqueous solution containing the ferrous hydroxide colloid while heating and stirring to subject the ferrous hydroxide colloid to oxidation reaction, thereby producing magnetite particles as black magnetic iron oxide. In the case where the divalent metal other than Fe is added similarly to the above co-precipitation method, there can be obtained spinel iron oxide particles containing the added metal. Further, the desired magnetic iron oxide fine particles can also be produced by suitably combining and controlling the reaction conditions.

The water-washing of the colloid aqueous solution containing the magnetic iron oxide fine particles may be performed by an ordinary method.

The thus obtained colloid aqueous solution of the magnetic iron oxide fine particles is then subjected to solid-liquid separation by a repeated decantation method, a method of passing the aqueous solution under pressure through a membrane filter, a filtering and water-washing method using a nutsche, or a method using a centrifugal separator, thereby producing the magnetic iron oxide fine particles.

Next, the thus obtained magnetic iron oxide fine particles are mixed with ultrapure water and re-dispersed therein using an ultrasonic dispersing apparatus, and then the resultant colloid aqueous solution is diluted with ultrapure water to control the concentration thereof to 5 to 50 mg/mL and further is treated with sodium hydroxide to control a zeta potential thereof to not more than −20 mV, thereby producing the pharmaceutical raw material according to the first aspect of the present invention, in which the magnetic iron oxide fine particles are monodispersed in a sterile water.

The pharmaceutical raw material according to the second aspect of the present invention is produced as follows. That is, in the co-precipitation method, for example, an aqueous alkali solution is added under stirring to a mixed aqueous solution containing 1 mol of an aqueous ferrous (Fe(II)) salt solution and 2 mol of an aqueous ferric (Fe(III)) salt solution under 50 to 200 mg/mL of a concentration of sum of a divalent metal salt including ferric (Fe(III)) salt, Mg salt, etc. and ferric (Fe(III)) salt, to cause a co-precipitation reaction between Fe(II) and 2Fe(III), thereby producing magnetite particles as black spinel-type magnetic iron oxide. Then, the magnetic iron oxide fine particles are mixed with ultrapure water, and re-dispersed therein using an ultrasonic dispersing apparatus, and then the resultant colloid aqueous solution is diluted with ultrapure water to control the concentration thereof to 5 to 50 mg/mL, thereby producing the pharmaceutical raw material according to the second aspect of the present invention in which the flocculated particles composed of the magnetic iron oxide fine particles are dispersed in a sterile water.

The dried product according to the third aspect of the present invention is produced by adding ultrapure water to the magnetic iron oxide fine particles and re-dispersing the particles therein using an ultrasonic dispersing apparatus. In this case, it is important to control the pH of the water dispersion to the range of from 9 to less than 12 by adding sodium hydroxide or a buffer thereto.

When the pH of the water dispersion is less than 9, the magnetic iron oxide fine particles tend to be deteriorated in dispersing condition, resulting in poor re-dispersing property after drying. On the other hand, when the pH of the water dispersion is not less than 12, the amount of salts dissolved in the water dispersion tends to be excessively increased.

Next, the water dispersion containing the magnetic iron oxide fine particles is dried to obtain the pharmaceutical raw material kept in a sterile condition. The drying of the water dispersion is preferably performed under reduced pressure, for example, by a freeze-drying method, in the consideration of preventing oxidation of the magnetic particles and good re-dispersing property of the obtained dried particles in water. The thus obtained dried product of the magnetic iron oxide fine particles has a water content of usually not more than 4% by weight, preferably not more than 2% by weight.

The concentration of the magnetic iron oxide fine particles in the water dispersion before conducting the drying method is suitably controlled to usually 5 to 50 mg/mL, preferably 10 to 40 mg/mL. When the concentration of the magnetic iron oxide fine particles in the water dispersion is more than 50 mg/mL, the magnetic iron oxide fine particles tend to be coagulated together owing to large influence of van der Waals force acting between the particles. When the concentration of the magnetic iron oxide fine particles in the water dispersion is less than 5 mg/mL, the pharmaceutical raw material having such a low content of the magnetic iron oxide fine particles tends to be unsuitable for actual use.

For example, upon the freeze-drying, the water dispersion is frozen at a temperature of usually not more than −20° C. and preferably not more than −40° C.

The pharmaceutical raw material of the third aspect of the present invention may be produced by adding a frozen product of the magnetic iron oxide fine particles to water (for example, ultrapure water) whose pH is controlled to not less than 9 by adding sodium hydroxide or a buffer thereto, and dispersing the obtained mixture using an ultrasonic dispersing apparatus, a homomixer, etc., to allow the frozen product to return to the colloid condition (water dispersion) before freezing. The thus obtained water dispersion of the magnetic iron oxide fine particles has a pH value of usually not less than 9.0 and an electrical conductivity of usually 50 to 400 µS.

The pharmaceutical raw material of the present invention may be used in various applications, for example, DDS as a method of delivering drugs, CT diagnosis used in roentgen or MRI (magnetic resonance), medical treatments such as thermotherapy, etc.

The pharmaceutical raw material of the present invention may be used in the above various applications by causing the magnetic iron oxide fine particles contained therein to be uniformly dispersed in and supported on a biocompatible substance.

Examples of the biocompatible substance may include substances used in ordinary drugs such as a phospholipid, a protein and water-soluble polymers.

As a result of the present inventors' earnest study, a superparamagnetism of the magnetic iron oxide fine particles as magnetic particles has been noticed, so that it has been found that a (mono)disperse colloid aqueous solution of the superparamagnetic iron oxide particles exhibit a good dispersion stability under specific conditions.

The superparamagnetism can be exhibited by a ferromagnetic material having a coercive force of zero. That is, in the case of the ferromagnetic particles having a large particle size notwithstanding a single domain structure thereof, when an external magnetic field is applied thereto for magnetizing the particles and then released therefrom, a residual magnetization is generated therein. On the other hand, when the ferromagnetic particles are decreased in particle size up to extremely fine particles, a coercive force thereof is decreased to finally zero. As a result, although such fine ferromagnetic particles are magnetized upon applying an external magnetic field thereto, if once the external magnetic field is released therefrom, no residual magnetization remains therein. This phenomenon is caused by thermal agitation effect, and such fine ferromagnetic particles are referred to as a "superparamagnetic material".

The pharmaceutical raw material of the present invention is free from coagulation of the magnetic particles contained therein even when approaching thereto a permanent magnet having a surface magnetic flux of 10 mT (100 Gauss), and therefore, can provide a monodisperse colloid aqueous solution exhibiting a good dispersion stability for a long period of time. This phenomenon might be considered to be inconsistent with such a fact that the magnetic iron oxide particles are made of a ferromagnetic material having a saturation magnetization of 50 to 90 $Am^2/kg$. However, the saturation magnetization value means a magnetization value per unit weight as measured with respect to the particles of magnetic iron oxide. Since the total number of the particles per unit weight is increased with decrease in particle size thereof, the magnetization value per one particle becomes smaller with the decrease in particle size thereof. Therefore, the magnetization value per one monodispersed superparamagnetic iron oxide particle is necessarily small, so that the magnetic particles can be prevented from suffering from magnetic coagulation therebetween and adverse influence by external magnetic field, and, therefore, kept in a stable dispersed condition.

Also, the reason for using the magnetic-particles made of superparamagnetic iron oxide is that the iron oxide has a good biocompatibility. The finer particles can be more readily egested from living bodies.

Meanwhile, the magnetic iron oxide fine particles which are merely uniformly dispersed in the biocompatible substance, tend to lack in magnetic properties required for magnetic particle-containing drugs. However, when the magnetic iron oxide fine particles are (mono)dispersed in the biocompatible substance in the drug-making process, the particles are flocculated together when granulated into drugs, thereby forming composite particles capable of exhibiting a ferromagnetism. This phenomenon can be explained by referring to such a known phenomenon that even superparamagnetic particles can exhibit a shape magnetic anisotropy when linked together into beads-like shape, and as a result, show a ferromagnetism owing to increase in coercive force thereof. That is, when the superparamagnetic iron oxide particles are uniformly dispersed and mixed in the biocompatible substance to form the composite material, and the thus obtained composite material is granulated into a desired size, the magnetic properties of the resultant granulated particles are varied depending upon the number of the magnetic particles contained in the respective granulated particles as well as the configuration of the granulated particles. Thus, even when using the superparamagnetic particles, the magnetic properties required for magnetic particle-containing drugs can be imparted thereto.

When the pharmaceutical raw material of the present invention is applied to a pyrogen of an exothermic agent, for example, in thermotherapy for cancers, there may also be used liposome-like composite particles each constituted from a core composed of an flocculate of a plurality of the magnetic iron oxide particles and a shell having a double film structure made of phospholipid and cationic lipid.

Further, the present inventors have noticed a superparamagnetism of the magnetic iron oxide fine particles as magnetic particles and have found conditions for producing a dried product of the superparamagnetic iron oxide particles.

The dried product according to the present invention can be stored while being kept in a sterile condition and can be readily re-dispersed in water.

Thus, since the pharmaceutical raw material of the present invention is in the form of a (mono)disperse colloid sterile aqueous solution of the magnetic iron oxide fine particles, there can be readily produced drugs composed of a composite material obtained by uniformly dispersing the magnetic particles in the biocompatible substance. In addition, since a solution containing no surfactant, etc., is used as a raw drug, adverse influence on safety to living bodies can be minimized.

Also, the granulated particles produced from the fine magnetic particles can be imparted with good ferromagnetic properties by controlling the flocculate condition of the fine particles in a granulation step of the drug-making process.

Further, the magnetic particles can be readily egested from living bodies after dosage thereof owing to ultrafine particles.

In the case where pharmaceutical raw material of the present invention is in the form of a dried product of the magnetic iron oxide fine particles which can be re-dispersed in water, the pharmaceutical raw material is free from growth of fungi upon storage, and the sterile condition thereof can be relatively readily maintained and controlled, so that there can be readily produced drugs composed of a composite material obtained by uniformly dispersing the magnetic particles in the biocompatible substance. In addition, since a solution containing no surfactant, etc., is used as a raw drug, adverse influence on safety to living bodies can be minimized.

Furthermore, since a solution containing no surfactant, etc., is used as a raw drug and the magnetic particles contained therein can be readily egested from living bodies after dosage thereof owing to ultrafine particles, there can be provided such a raw drug which is free from any problems such as safety after dosage to human bodies, and metabolism and egestion.

EXAMPLES

The present invention is described in more detail by Examples. However, the Examples are only illustrative and not intended to limit the scope of the present invention.

Various properties were evaluated by the following methods.

(1) The structural analysis of the product was performed using an X-ray diffractometer, and the average particle diameter of the product was calculated from a true half value-width observed at (311) of an X-ray diffraction curve according to the Scherrer's formula.

(2) The particle size distribution of the particles was observed using a transmission electron microscope TEM. Further, the digitizer analysis of the particles was performed to measure an average particle diameter and a standard deviation value thereof. From these measured values, the variation coefficient was calculated according to the following formula:

Variation coefficient (%)=(standard deviation)×100/ (average particle diameter)

(3) The $Fe^{2+}$ content was measured by chelate titration method.

(4) The particle diameter of the flocculated particles was measured by a dynamic light scattering method using a particle size distribution meter "FPAR-1000" manufactured by Otsuka Denshi Co., Ltd.

(5) The specific surface area was measured by a BET method.

(6) The magnetic properties were measured using a vibration sample type magnetometer "VSM" by applying a magnetic field of 10 k/4 πkA/m thereto.

(7) The pharmaceutical raw material was subjected to sterile test using a membrane filter method on the basis of Japan pharmacopoeia, and endotoxin test for examining the presence or absence of wrecks of fungi.

(8) The electrical conductivity of the product was measured using an electrical conductivity meter.

(9) The occurrence of magnetic coagulation of the magnetic particles in the pharmaceutical raw material was determined using a permanent magnet having a surface magnetic flux of 100 Gauss.

(10) The zeta ($\zeta$) potential was measured using "ELS-6000" manufactured by Otsuka Denshi Co., Ltd.

<Examples for the First Aspect of the Present Invention>

Example 1

In the following Examples, there were used a 5000 mL reaction vessel equipped with a stirrer and a heater, a raw iron salt and sodium hydroxide as guaranteed reagents, and ion-exchanged water.

(1) Step for Production of Superparamagnetic Iron Oxide Particles:

500 mL of a 0.5 M ferrous chloride aqueous solution and 1000 mL of a 0.5 M ferric chloride aqueous solution were charged into the reaction vessel and mixed with each other under stirring to prepare a mixed aqueous solution containing the ferrous salt and the ferric salt, followed by heating the mixed aqueous solution. After the temperature of the mixed iron salt aqueous solution reached 80° C., 2300 mL of a previously prepared 1.0 M sodium hydroxide aqueous solution was added to the mixed aqueous solution while stirring. After completion of adding the sodium hydroxide aqueous solution, the resultant mixed aqueous solution was continuously stirred for 60 min while maintaining the temperature thereof at 80° C., thereby producing a black colloid aqueous solution which was sensitive to a magnet.

A part of the thus obtained colloid aqueous solution was sampled and then subjected to water-washing and filtration to obtain a paste. The obtained paste was freeze-dried to obtain particles. As a result of analyzing the obtained particles, it was confirmed that the particles had a spinel-type crystal structure having an average particle diameter of 10 nm, and a variation coefficient of particle size distribution thereof was 7%. Also, it was confirmed that the particles were magnetic iron oxide particles having a $Fe^{2+}$ content of 17.5 mol %. As to the magnetic properties, it was confirmed that the particles were superparamagnetic iron oxide particles having a saturation magnetization σs of 68 $Am^2$/kg and a coercive force Hc of 0.4 kA/m.

(2) Step for Purification of Colloid Particles:

The thus produced black colloid aqueous solution contained soluble salts by-produced upon the synthesis reaction for producing the black colloid particles. Therefore, the black colloid aqueous solution was subjected to decantation using ion-exchanged water to water-wash and remove the by-produced salts therefrom, thereby obtaining a purified black colloid aqueous solution.

(3) Step for Purification of Pharmaceutical Raw Material (Replacement with Ultrapure Water):

100 mL of the black colloid aqueous solution which remained after sampling the part of the aqueous solution for evaluating the properties of the product, was sampled while intimately stirring. The thus sampled colloid aqueous solution was subjected to solid-liquid separation using a centrifugal separator to remove the dispersing medium therefrom. Thereafter, the obtained solid was mixed with an equiamount of ultrapure water, and re-dispersed therein using an ultrasonic dispersing apparatus, thereby completing one cycle of the purification treatment. The colloid aqueous solution was repeatedly subjected to 5 cycles of the purification treatment, thereby replacing the dispersing medium of the colloid aqueous solution with ultrapure water. Next, the colloid aqueous solution was mixed with ultrapure water to adjust a concentration of the colloid particles therein to 22 mg/mL, and then a 0.1 N sodium hydroxide aqueous solution was added to the colloid aqueous solution while dispersing the aqueous solution using an ultrasonic dispersing apparatus to adjust a zeta potential thereof to −55 mV. After 60 min, operation of the ultrasonic dispersing apparatus was stopped, and the colloid aqueous solution was allowed to stand for 360 min.

As a result, it was confirmed that no precipitate was produced in the thus obtained colloid aqueous solution, and the magnetic particles contained therein were free from magnetic coagulation even when using a permanent magnet having a surface magnetic flux of 100 Gauss. Also, as a result of the toxicity test and endotoxin test, it was confirmed that the colloid aqueous solution was a negative for each of toxicity and endotoxin (specifically, a plate count of less than $1 \times 10^{-6}$/unit and an endotoxin value of not more than 0.25 EU/mL). Thus, 150 mL of a monodisperse colloid sterile aqueous solution of the superparamagnetic iron oxide particles was produced.

The thus obtained colloid aqueous solution had a pH of 9.7 and an electrical conductivity of 210 μS.

Example 2

The same procedure for the synthesis step (1) for producing the superparamagnetic iron oxide particles as defined in Example 1 was conducted except that 300 mL of a 0.5 M ferrous chloride aqueous solution and 200 mL of a 0.5 M magnesium sulfate aqueous solution were used, and the same procedures for the steps (2) and (3) as defined in Example 1 were conducted under the same conditions, thereby producing a pharmaceutical raw material containing the superparamagnetic iron oxide particles in an amount of 20 mg/mL.

A part of the thus obtained colloid aqueous solution was sampled and then subjected to water-washing and filtration to obtain a paste. The paste was freeze-dried to obtain particles. As a result of analyzing the obtained particles, it was confirmed that the particles had a spinel-type crystal structure having an average particle diameter of 8 nm, and a variation coefficient of particle size distribution thereof was 7%. Also, it was confirmed that the particles were magnetic iron oxide particles having a $Fe^{2+}$ content of 14 mol % and a $Mg^{2+}$ content of 5.5 mol %. As to the magnetic properties, it was conformed that the particles were superparamagnetic iron oxide particles having a saturation magnetization σs of 63 $Am^2$/kg and a coercive force Hc of 0.2 kA/m.

Further, the dispersing medium of the colloid aqueous solution was replaced with ultrapure water by the same method as defined in Example 1. Next, the resultant colloid dispersion was diluted with ultrapure water to adjust a concentration thereof to 20 mg/mL, and simultaneously a 0.1 N sodium hydroxide aqueous solution was added to the colloid dispersion to adjust a zeta potential thereof to −45 mV. Further, by using a permanent magnet having a surface magnetic flux of 100 Gauss, it was confirmed that the magnetic particles contained in the colloid dispersion were free from magnetic coagulation. Also, as a result of the endotoxin test, it was confirmed that the colloid dispersion was a negative for endotoxin (specifically, a plate count of less than $1 \times 10^{-6}$/unit and an endotoxin value of not more than 0.25 EU/mL). Thus, 150 mL of a monodisperse colloid sterile aqueous solution of the superparamagnetic iron oxide particles was produced.

The thus obtained colloid aqueous solution had a pH of 9.8 and an electrical conductivity of 240 µS.

<Examples for the Second Aspect of the Present Invention>

Example 3

In the following Examples, there were used a 5000 mL reaction vessel equipped with a stirrer and a heater, a raw iron salt and sodium hydroxide as guaranteed reagents, and ion-exchanged water.

(1) Step for Synthesis of Superparamagnetic Iron Oxide Particles:

75 mL of a 1.5 M ferrous chloride aqueous solution and 225 mL of a 1.0 M ferric chloride aqueous solution were charged into the reaction vessel and mixed with each other under stirring to prepare a mixed aqueous solution containing the ferrous salt and the ferric salt, followed by heating the mixed aqueous solution. When the temperature of the mixed iron salt aqueous solution reached 60° C., 189 mL of a previously prepared 6.0 M sodium hydroxide aqueous solution and 11 mL of pure water were added to the mixed aqueous solution while stirring. After completion of adding the aqueous solution and pure water, the resultant mixed aqueous solution was continuously stirred for 60 min while maintaining the temperature thereof at 60° C., thereby producing a black colloid aqueous solution which was sensitive to a magnet.

A part of the thus obtained colloid aqueous solution was sampled and then subjected to water-washing and filtration to obtain a paste. The paste was freeze-dried to obtain particles. As a result of analyzing the obtained particles, it was confirmed that the particles had a spinel-type crystal structure having an average particle diameter of 11 nm, and a variation coefficient of particle size distribution of primary particles thereof was 7%. Also, it was confirmed that the particles were magnetic iron oxide fine particles having a $Fe^{2+}$ content of 13.8 mol %. As to the magnetic properties, it was confirmed that the particles were superparamagnetic iron oxide particles having a saturation magnetization as of 64 $Am^2$/kg and a coercive force Hc of 2.0 kA/m. Further, it was confirmed that the particle diameter of the flocculated particles was 85 nm.

(2) Step for Purification of Colloid Particles:

The thus produced black colloid aqueous solution contained soluble salts by-produced upon the synthesis reaction for producing the black colloid particles. Therefore, the black colloid aqueous solution was subjected to decantation using ion-exchanged water to water-wash and remove the by-produced salts therefrom, thereby obtaining a purified black colloid aqueous solution.

(3) Step for Purification of Pharmaceutical Raw Material (Replacement with Ultrapure Water):

100 mL of the black colloid aqueous solution which remained after sampling the part of the aqueous solution for evaluating the properties of the product, was sampled while intimately stirring. The thus sampled colloid aqueous solution was subjected to solid-liquid separation using a centrifugal separator to remove the dispersing medium therefrom. Thereafter, the obtained solid was mixed with an equiamount of ultrapure water, and re-dispersed therein using an ultrasonic dispersing apparatus, thereby completing one cycle of the purification treatment. The colloid aqueous solution was repeatedly subjected to 5 cycles of the purification treatment, thereby replacing the dispersing medium of the colloid aqueous solution with ultrapure water. Next, the colloid aqueous solution was mixed with ultrapure water to adjust a concentration of the colloid particles therein to 22 mg/mL, and then a 0.1 N sodium hydroxide aqueous solution was added to the colloid aqueous solution while dispersing the aqueous solution using an ultrasonic dispersing apparatus to adjust a zeta potential thereof to −55 mV. After 60 min, operation of the ultrasonic dispersing apparatus was stopped, and the colloid aqueous solution was allowed to stand for 360 min.

As a result, it was confirmed that no precipitate was produced in the thus obtained colloid aqueous solution, and the magnetic particles contained therein were free from magnetic coagulation even when using a permanent magnet having a surface magnetic flux of 100 mT (100 Gauss). Also, as a result of the toxicity test and endotoxin test, it was confirmed that the colloid aqueous solution was a negative for each of toxicity and endotoxin (specifically, a plate count of less than $1 \times 10^{-6}$/unit and an endotoxin value of not more than 0.25 EU/mL). Thus, 150 mL of a monodisperse colloid sterile aqueous solution containing flocculated particle composed of the superparamagnetic iron oxide particles was produced.

The thus obtained colloid aqueous solution contained the magnetic iron oxide fine particles in an amount of 20 mg/mL, and had a pH of 9.7 and an electrical conductivity of 210 µS.

Example 4

The same procedure for the synthesis step (1) for producing the superparamagnetic iron oxide particles as defined in Example 3 was conducted except that 150 mL of a 0.5 M ferrous chloride aqueous solution, 200 mL of a 0.5 M magnesium sulfate aqueous solution and 225 mL of a 1.0 M ferric chloride aqueous solution were used, and the same procedures for the steps (2) and (3) as defined in Example 3 were conducted under the same conditions, thereby producing a pharmaceutical raw material containing the magnetic iron oxide fine particles in an amount of 20 mg/mL.

A part of the thus obtained colloid aqueous solution was sampled and then subjected to water-washing and filtration to obtain a paste. The paste was freeze-dried to obtain particles. As a result of analyzing the obtained particles, it was confirmed that the particles had a spinel-type crystal structure having an average particle diameter of 12 nm, and a variation coefficient of particle size distribution of primary particles thereof was 7%. Also, it was confirmed that the particles were magnetic iron oxide fine particles having a $Fe^{2+}$ content of 10 mol % and a $Mg^{2+}$ content of 3.5 mol %. As to the magnetic properties, it was confirmed that the particles were superparamagnetic iron oxide particles having a saturation magnetization σs of 63 $Am^2$/kg and a coercive force Hc of 1.4 kA/m. Also, it was confirmed that the particle diameter of the flocculated particles was 125 nm.

Further, the dispersing medium of the colloid aqueous solution was replaced with ultrapure water by the same method as defined in Example 3. The resultant colloid aqueous solution was diluted with ultrapure water to adjust a concentration thereof to 20 mg/mL, and simultaneously a 0.1 N sodium hydroxide aqueous solution was added to the colloid aqueous solution to adjust a zeta potential thereof to −45 mV. Further, by using a permanent magnet having a surface magnetic flux of 100 mT (100 Gauss), it was confirmed that the magnetic particles contained in the colloid aqueous solution were free from magnetic coagulation. Also, as a result of the endotoxin test, it was confirmed that the colloid aqueous solution was a negative for endotoxin (specifically, a plate count of less than $1 \times 10^{-6}$/unit and an endotoxin value of not more than 0.25 EU/mL). Thus, 150 mL of a monodisperse colloid sterile aqueous solution containing flocculated particle composed of the superparamagnetic iron oxide particles was produced.

The thus obtained colloid aqueous solution had a pH of 9.8 and an electrical conductivity of 250 μS.

<Examples for the Third Aspect of the Invention>

Example 5

In the following Examples, there were used a 5000 mL reaction vessel equipped with a stirrer and a heater, a raw iron salt and sodium hydroxide as guaranteed reagents, and ion-exchanged water.

(1) Step for Synthesis of Magnetic Iron Oxide Fine Particles:

75 mL of a 1.5 M ferrous chloride aqueous solution and 225 mL of a 1.0 M ferric chloride aqueous solution were charged into the reaction vessel and mixed with each other under stirring to prepare a mixed aqueous solution containing the ferrous salt and the ferric salt, followed by heating the mixed aqueous solution. When the temperature of the mixed iron salt aqueous solution reached 60° C., 189 mL of a previously prepared 6.0 M sodium hydroxide aqueous solution and 11 mL of pure water were added to the mixed aqueous solution while stirring. After completion of adding the aqueous solution and pure water, the resultant mixed aqueous solution was continuously stirred for 60 min while maintaining the temperature thereof at 60° C., thereby producing a black colloid aqueous solution which was sensitive to a magnet.

A part of the thus obtained colloid aqueous solution was sampled and then subjected to water-washing and filtration to obtain a paste. The paste was freeze-dried to obtain particles. As a result of analyzing the obtained particles, it was confirmed that the particles had a spinel-type crystal structure having a BET specific surface area of 92.0 m²/g and an average particle diameter of 11 nm, and a variation coefficient of particle size distribution of primary particles thereof was 7%. Also, it was confirmed that the particles were magnetic iron oxide fine particles having a $Fe^{2+}$ content of 13.8 mol %. As to the magnetic properties, it was confirmed that the particles were magnetic iron oxide fine particles having a saturation magnetization σs of 64 Am²/kg and a coercive force Hc of 2.0 kA/m. Further, it was confirmed that the particle diameter of the flocculated particles was 85 nm.

(2) Step for Purification of Colloid Particles:

The thus produced black colloid aqueous solution contained soluble salts by-produced upon the synthesis reaction for producing the black colloid particles. Therefore, the black colloid aqueous solution was subjected to decantation using ultrapure water to water-wash and remove the by-produced salts therefrom, and further a 0.1 N sodium hydroxide aqueous solution was added thereto, thereby obtaining a purified black colloid aqueous solution having a zeta potential of −55 mV, a pH of 9.7 and an electrical conductivity of 210 μS.

(3) Step for Production of Pharmaceutical Raw Material (Drying):

The colloid aqueous solution was subjected to filtration under reduced pressure using a nutsche to separate paste-like magnetic iron oxide fine particles therefrom. Thereafter, the thus separated magnetic iron oxide fine particles were dried using "PREFREEZER PFM-1000" manufactured by Tokyo Rika Kikai Co., Ltd., thereby obtaining a dried product thereof.

As to the magnetic properties of the thus obtained dried product of the magnetic iron oxide fine particles, it was confirmed that a BET specific surface area thereof was 92.0 m²/g, a saturation magnetization σs thereof was 64 Am²/kg, a coercive force Hc thereof was 2.0 kA/m, and a water content thereof was 10% by weight.

Example 6

The same procedure for the synthesis step (1) for producing the magnetic iron oxide fine particles as defined in Example 5 was conducted except that 100 mL of a 1.5 M ferrous chloride aqueous solution, 200 mL of a 0.5 M magnesium sulfate aqueous solution and 225 mL of a 1.0 M ferric chloride aqueous solution were used, and the same procedures for the steps (2) and (3) as defined in Example 5 were conducted under the same conditions, thereby producing a pharmaceutical raw material containing the magnetic iron oxide fine particles.

As a result of analyzing the obtained particles, it was confirmed that the particles had a spinel-type crystal structure having an average particle diameter of 10 nm, and a variation coefficient of particle size distribution thereof was 7%. Also, it was confirmed that the particles were magnetic iron oxide particles having a $Fe^{2+}$ content of 8 mol %, a $Mg^{2+}$ content of 5.5 mol % and a BET specific surface area of 132 m²/g. As to the magnetic properties, it was confirmed that the particles were magnetic iron oxide fine particles having a saturation magnetization as of 55 Am²/kg and a coercive force Hc of 0.8 kA/m.

USE EXAMPLE

The dried product of the magnetic iron oxide fine particles obtained in Example 5 was added to water whose pH was adjusted to 10.0 by adding a 0.1 N sodium hydroxide aqueous solution thereto, and the resultant mixture was dispersed for about 20 min using a homomixer, thereby obtaining such a colloid solution in which the magnetic iron oxide fine particles were dispersed in water.

As a result, it was confirmed that the thus obtained colloid aqueous solution had a pH of 9.7 and an electrical conductivity of 210 μS.

Further, as a result of testing the colloid aqueous solution by a membrane filter method, it was confirmed that the solution was kept in a sterile condition. More specifically, it was confirmed that the colloid aqueous solution had a plate count of less than $1 \times 10^{-6}$/unit and an endotoxin value of not more than 0.25 EU/mL.

What is claimed is:

1. A pharmaceutical raw material consisting of:
  magnetic iron oxide fine particles having an average particle diameter of 5 to 30 nm, a saturation magnetization of 50 to 90 Am$^2$/kg, a coercive force of 0 to 1.6 kA/m, a variation coefficient of particle size distribution of not more than 10% and composed of a composition with a spinet structure which is represented by the formula:

$$MOFe_2O_3$$

wherein M is a divalent metal represented by the formula: MOFe$_2$O$_3$, is Fe, Mg, or Fe and Mg with the proviso that a total amount of Fe and Mg is not more than 1 mol based on 1 mol of Fe$_2$O$_3$, and ultrapure water, said material having a pH of not less than 9.0 and being in the form of a monodisperse colloid sterile aqueous solution containing 5 to 50 mg/mL of the magnetic iron oxide fine particles.

2. A pharmaceutical raw material according to claim 1, wherein said aqueous colloid solution has a pH of 9.0 to 11.0 and an electrical conductivity of not less than 100 μS.

3. A pharmaceutical raw material according to claim 1, which is a dried product produced from the colloid sterile aqueous solution containing the magnetic iron oxide fine particles.

4. A pharmaceutical raw material according to claim 3, wherein said magnetic iron oxide fine particles have a variation coefficient of particle size distribution of not more than 10%.

5. A pharmaceutical raw material consisting of:

magnetic iron oxide fine particles having an average particle diameter of 5 to 30 nm, a saturation magnetization of 50 to 90 Am$^2$/kg, a coercive force of 0 to 1.6 kA/m, a variation coefficient of particle size distribution of not more than 10% and composed of a composition with a spinet structure which is represented by the formula:

$$MOFe_2O_3$$

wherein M is a divalent metal represented by the formula: MOFe$_2$O$_3$, is Fe, Mg, or Fe and Mg with the proviso that a total amount of Fe and Mg is not more than 1 mol based on 1 mol of Fe$_2$O$_3$, an endotoxin in an amount of not more than 0.25 EU/mL; and ultrapure water, said material having a pH of not less than 9.0 and being in the form of a monodisperse colloid sterile aqueous solution containing 5 to 50 mg/mL of the magnetic iron oxide fine particles.

6. A pharmaceutical raw material consisting of flocculated particles composed of primary particles of the magnetic iron oxide fine particles, having an average particle diameter of 5 to 30 nm, a saturation magnetization of 35 to 90 Am$^2$/kg, a coercive force of 0 to 6.0 kA/m, a variation coefficient of particle size distribution of not more than 10% and composed of a composition with a spinel structure which is represented by the formula:

$$MOFe_2O_3$$

wherein M is a divalent metal represented by the formula: MOFe$_2$O$_3$, is Fe, Mg, or Fe and Mg with the proviso that a total amount of Fe and Mg is not more than 1 mol based on 1 mol of Fe$_2$O$_3$, and ultrapure water, said material having a pH of not less than 9.0 and being in the form of a monodisperse colloid sterile aqueous solution containing 5 to 50 mg/mL of the magnetic iron oxide fine particles, said flocculated particles having a particle diameter of 30 to 200 nm, and said pharmaceutical raw material being in the form of a colloid sterile aqueous solution in which the flocculated particles composed of the magnetic iron oxide fine particles are dispersed.

7. A pharmaceutical raw material according to claim 6, wherein said aqueous colloid solution has a zeta potential of not more than −20 mV and an electrical conductivity of not less than 50 μS.

8. A pharmaceutical raw material consisting of:

magnetic iron oxide fine particles having an average particle diameter of 5 to 30 nm, a saturation magnetization of 50 to 90 Am$^2$/kg, a coercive force of 0 to 1.6 kA/m, a variation coefficient of particle size distribution of not more than 10% and composed of a composition with a spinel structure which is represented by the formula:

$$MOFe_2O_3$$

wherein M is a divalent metal represented by the formula: MOFe$_2$O$_3$, is Fe, Mg, or Fe and Mg with the proviso that a total amount of Fe and Mg is not more than 1 mol based on 1 mol of Fe$_2$O$_3$, at least one member selected from a phospholipid, a polysaccharide, a protein and a dextrin;

ultrapure water, said material having a pH of not less than 9.0 and being in the form of a monodisperse colloid sterile aqueous solution containing 5 to 50 mg/mL of the magnetic iron oxide fine particles.

9. A pharmaceutical raw material consisting of:

magnetic iron oxide fine particles having an average particle diameter of 5 to 30 nm, a saturation magnetization of 50 to 90 Am$^2$/kg, a coercive force of 0 to 1.6 kA/m, a variation coefficient of particle size distribution of not more than 10% and composed of a composition with a spinel structure which is represented by the formula:

$$MOFe_2O_3$$

wherein M is a divalent metal represented by the formula: MOFe$_2$O$_3$, is Fe, Mg, or Fe and Mg with the proviso that a total amount of Fe and Mg is not more than 1 mol based on 1 mol of Fe$_2$O$_3$, wherein said magnetic iron oxide fine particles are in the form of a composite material comprising the magnetic iron oxide fine particles and at least one member selected from a phospholipid, a polysaccharide, a protein and a dextrin, and ultrapure water, said material having a pH of not less than 9.0 and being in the form of a monodisperse colloid sterile aqueous solution containing 5 to 50 mg/mL of the magnetic iron oxide fine particles.

* * * * *